Figure 1:
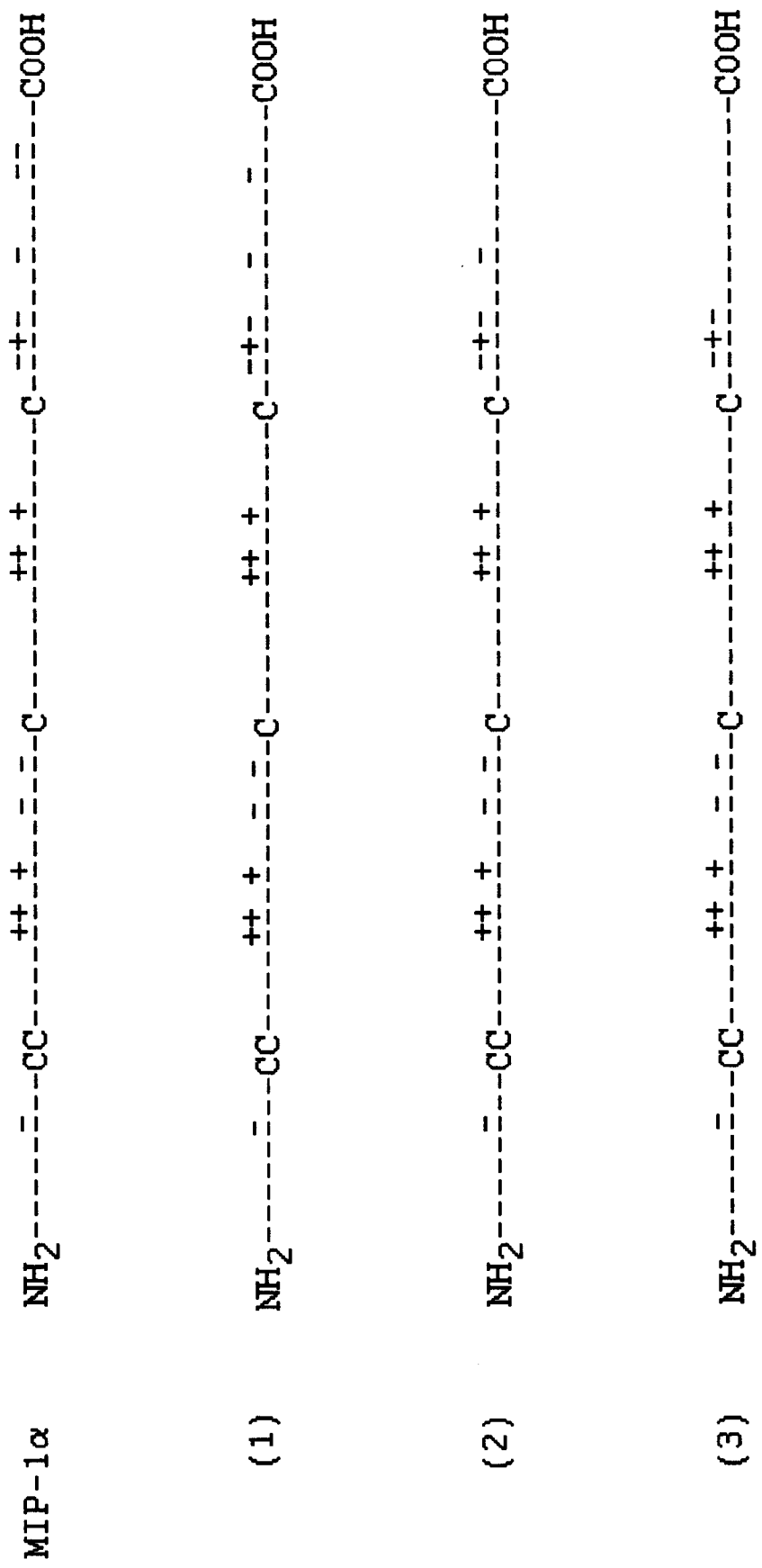

United States Patent [19]
Graham et al.

[11] Patent Number: 5,936,067
[45] Date of Patent: Aug. 10, 1999

[54] MACROPHAGE INFLAMMATORY PROTEIN VARIANTS

[75] Inventors: Gerard Graham; Ian Pragnell, both of Glasgow, United Kingdom

[73] Assignee: Genetics Institute, Inc., Cambridge, Mass.

[21] Appl. No.: 08/535,116

[22] PCT Filed: Apr. 19, 1994

[86] PCT No.: PCT/GB94/00822

§ 371 Date: Jan. 29, 1996

§ 102(e) Date: Jan. 29, 1996

[87] PCT Pub. No.: WO94/24285

PCT Pub. Date: Oct. 27, 1994

[30] Foreign Application Priority Data

Apr. 19, 1993 [GB] United Kingdom .................. 9308060

[51] Int. Cl.$^6$ .......................... C07K 14/52; C12N 15/19
[52] U.S. Cl. .................. 530/351; 424/85.1; 536/23.5; 435/69.5; 435/69.1; 530/350; 530/395
[58] Field of Search ................. 530/356, 351, 530/395; 514/2, 8, 12; 424/85.1; 435/69.1, 69.5

[56] References Cited

U.S. PATENT DOCUMENTS 5,556,767  9/1996  Rosen et al. ........................... 435/69.1

FOREIGN PATENT DOCUMENTS

WO 91/04274  4/1991  WIPO.
WO 92/05198  4/1992  WIPO.
WO 93/13206  7/1993  WIPO.

OTHER PUBLICATIONS

Graham et al, *GMBO* 15(23) 1996, pp. 6505–6515.
Koopmann et al, *JBC* 273(15) 1797, pp. 10103–10107.
Frommel et al, *J Mol Evol.* 1985, vol. 21, pp. 233–257.
Bowie et al, Science 1990, vol. 247, pp. 1306–1310.
The Folding Protein Problem, ed. merz, 1994, Ngo et al, pp. 433–434, 492–495.
Graham et al., Growth Factors 7(2):151 (1992).
Mantel et al., Proc. Nat'l. Acad. Sci. USA 90:2232 (1993).
Graham et al., J. Biol. Chem. 269:4974 (1994).
Wright et al., Biological Abstracts, Reviews–Reports–Meetings 35: No. 106933 (1988).
Janowska–Wieczorek et al., Biological Abstracts, Reviews–Reports–Meetings 33:No. 61402 (1987).
Guigon et al., Chem. Abstracts 96:36 (Abstract No. 115633h) (1982).
Guigon et al., Cancer Res. 42:638 (1982).
Ralph et al., Cancer Res. 37:546 (1977).
Ralph et al., J. Immunol. 114(2):898 (1975).
Saukkonon et al., J. Exp. Med. 171:439 (1990).
Wolpe and Cerami, FASEB J. 3:2565 (1989).
Wolpe et al., Abstracts H141, J. Cell Biochem. Suppl. 0 (13 Part C):21 (1989).
Wolpe et al., J. Exp. Med 167:570 (1988).
Nakao et al., Mol. and Cell Biol. 10(7):3646 (1990).
Zipfel et al., J. Immunol. 142(5):1582 (1989).
Obaru et al., J. Biochem. 99:885 (1986).
Miller et al., J. Immunol. 143:2907 (1989).
Brown et al., J. Immunol. 142:679 (1989).
Lord et al., Brit. J. Haematology 34:441 (1976).
Wright et al., Leukemia Res. 4(6):537 (1980).
Dexter and White, Nature 344:380 (1990).
Wright et al., Cell Tissue Kinet, 18:193 (1985).
Lipes et al., Proc. Nat'l. Acad. Sci. USA 85:9704 (1988).
Pragnell et al., Blood 72(1):196 (1988).
Graham et al., Nature 344:442 (1990).

*Primary Examiner*—Garnette D. Draper
*Attorney, Agent, or Firm*—Scott A. Brown; Thomas J. DesRosier

[57] ABSTRACT

The present invention provides a Stem Cell Inhibitor (SCT) protein which comprises at least one amino acid alteration from its active form which protein does not significantly aggregate but which retains substantially unaltered stem cell inhibitory activity. The alteration is preferably a conservative substitution of a charged amino acid residue. Such proteins may be used in treating stem cells in a patient undergoing chemotherapy.

6 Claims, 1 Drawing Sheet

MACROPHAGE INFLAMMATORY PROTEIN VARIANTS

The present invention relates to variants of stem cell inhibitors.

The treatment of cancer with chemotherapeutic agents is designed to attack and destroy cells which are undergoing division within the body. A side effect of such treatment is thus the destruction of normal cells, particularly the stem cells of the haematopoietic system and the epithelial stem cells which line the scalp and gut. Radiation can also cause similar destruction of such cells.

It has been proposed that in order to improve the treatment of cancers by chemotherapy it would be desirable to protect stem cells from cell cycle specific cytotoxic drugs. WO89/10133 discloses a stem cell inhibitor and describes the use of the inhibitor in the treatment of cancers. The inhibitor may be administered to a patient in order to protect stem cells during chemotherapy.

Stem Cell Inhibitor (SCI), also known as MIP1-α is a peptide of about 8 kD which forms large self aggregates, the molecular weight of which is dependent upon the concentration of SCI/MIP1-α monomers (Graham et al, 1990, Nature 344;442, Wolpe & Cerami, 1989, FASEB J, 3; 2656). It has been found that SCI/MIP1-α has a native, aggregated molecular weight of about 100 kD at 0.1 mg/ml in physiological buffers such as PBS. It has been found that diluting SCI/MIP1-α to about 20–100 ng/ml or less will bring about disaggregation of this protein.

Human SCI/MIP1-α has been cloned by us (Graham et al (1992), Growth Factors 7;151–160). The cDNA has also been cloned by Nakao et al (1990, Mol. Cell, Biol., 10;3646–58) and called LD78β. A variant of the cDNA LD78α was also found, which has a very similar sequence. It differs by only 4 amino acid residues. The human cDNA and protein sequence of the factor cloned by us is shown is Seq. ID No. 1. The first 27 amino acids are a leader sequence. The mature protein starts at residue 28 (ala). The amino acid sequence of the variant found by Nakao et al is shown as Seq. ID No. 3. The leader sequence of the protein is one amino acid shorter and thus the mature protein starts at residue 27 (ala). The sequence of the murine homologue, upon which we have conducted our work, is also known and is very similar. It can be found for example in Graham et al (1994, J. Biol. Chem., 269; 4974–78).

It has been reported (Mantel et al, 1993, PNAS 90;2232) that monomeric SCI/MIP1-α is more active than the aggregated form in inhibiting in vitro and in vivo stem cell proliferation. In using SCI/MIP1-α in the treatment of humans it would be desirable to administer monomeric protein, not just from an activity point of view but also in order to provide reliable and reproducible formulations. However, it is likely that the low concentrations of SCI/MIP1-α which must be made in order to provide monomeric protein will be too low for use in practice.

We have now surprisingly found that it is possible to obtain SCI/MIP1-α variants which retain substantially the activity of the native protein but which do not form the same large aggregates. These mutants are stable as monomers or as small conglomerates (eg dimers or tetramers) at concentrations many fold higher than native SCI/MIP1-α. Thus for those variants which have activity comparable to native SCI/MIP1-α, the variants may have higher activity in vivo on a unit weight basis.

Accordingly, the present invention provides a Stem Cell Inhibitor protein which comprises at least one amino acid alteration from its native form which does not significantly aggregate but which retains substantially unaltered stem cell inhibitory activity. The protein may comprise either the full length stem cell inhibitor or the mature processed form lacking the leader sequence.

The invention also provides pharmaceutical compositions comprising a stem cell inhibitor according to the invention in combination with a pharmaceutically acceptable carrier or diluent, and optionally other therapeutic ingredients. The carrier(s) must be "acceptable" in the sense of being compatible with the other ingredients of the formulation and not deleterious to the recipients thereof.

The formulations include those suitable for parenteral (including subcutaneous, intramuscular, intravenous, intraperitoneal, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Suitable liquid carriers include phosphate buffered saline at a pH of between 7.0 and 8.0, for example 7.4. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use.

Preferred unit dosage formulations are those containing a daily dose or unit, daily sub-dose, or an appropriate fraction thereof, of an active ingredient.

Formulations of the SCI/MIP-1α proteins of the present invention preferably contain from 0.05 to 5 mg/ml of protein, for example 0.1 to 1.0 mg/ml. We have found that the solubility of the variants of the invention do vary although the maximum solubility of any one particular variant may be determined by simple titration by those of skill in the art.

The invention also provides such proteins and compositions for use in a method of treatment of the human or animal body.

The invention further provides a method for treating a subject who is to be exposed to an agent capable of killing dividing or cycling stem cells by administering to the subject an effective amount of a protein or composition according to the invention.

The subject may also be treated with a protein or composition according to the invention during or after chemotherapy. In the latter case, this will usually be for a period sufficient to allow clearance of the agent from the body.

The method of treatment according to the invention may be used in the treatment of solid tumours or leukemias. In the case of is treatment of leukemias, it is possible to treat a sample of the patients bone marrow which has been removed from the body while the patient is undergoing-treatment. The bone marrow is purged of cancer cells in the presence of a protein of composition according to the invention, and the treated marrow reintroduced into the patient.

Although the dose of the variant protein according to the invention will ultimately be at the discretion of the physician, taking into account the nature of the condition being treated and the state of the patient, effective doses may be in the range of from about 10 μg/kg body weight to about 5 mg/kg of variant protein, for example from about 50 to about 1000 μg/kg, eg about 500 μg/kg.

We have also found that SCI/MIP1-α can act to enhance the expansion of primitive haemopoietic cells in ex vivo cytokine driven stem cell expansion experiments. Thus, variant proteins of the invention may also be used in methods to expand stem cell populations removed from a patient ex vivo wherein such stem cells are brought into contact with growth factors and the variant proteins of the invention under conditions which allow the growth and expansion in numbers of the cells, prior to reintroduction into the same or another patient. Such a method could be used in bone marrow transplant proceedures whereby a limited number of starting cells obtained from a donor are expanded prior to transplantation, or in certain therapies where a sample of bone marrow is removed from a patient prior to treatment and reintroduced following treatment. Such therapies include the treatment of leukemias, or other tumours including solid tumours where damage to the bone marrow may occur. The concentration of the variant proteins required to produce suitable activity will be in the range of from about 1 to about 100 ng/ml, for example from about 10 to about 50 ng/ml.

A protein or composition according to the invention may also be used in the treatment of disorders caused by proliferation of stem cells, eg. psoriasis.

A protein according to the invention is preferably a protein which contains at least one change from the native protein resulting in the loss of of one of more charges on the protein, eg. by replacement of one or more charged amino acids.

The change may be as a result of a deletion or substitution or insertion. In the case of a deletion or insertion, single base deletions or insertions are generally preferred, in order to retain a structure similar to the native protein. However, deletions of insertions of more than this, eg or 2, 3, 4, 5 or more amino acids are possible. In the case of a substitution, it is preferably a conservative substitution, such as Asp to Asn or Glu to Gln.

In addition, fragments of native protein which retain their stem cell inhibitory activity but which exhibit the reduced tendency to aggregate are within the scope or the invention.

Preferably, the change to the protein is in the C-terminal region, eg within the last 20 or even last 10 amino acids. This may include C-terminal deletions.

More than one change to a native stem cell inhibitor protein may be made. For example, 2, 3, 4 or 5 charges may be made.

Another preferred region of the MIP1 protein which may be altered is the putative heparin binding region between amino acids 68 and 71 of Seq. ID No. 1. We have determined by experimentation and by comparison of this sequence with known heparin binding regions that this portion of MIP1 has heparin binding activity. Thus suitable amino acids which may be altered in accordance with the invention include one, two or three of 68(lys), 69(arg) and 71(arg). Such alterations may be made, if desired with an alteration to the c-terminal region of the MIP1 protein as described above.

Preferred stem cell inhibitor proteins of the invention are those based upon the human protein of Seq. ID. 2 or that of Seq. ID 3. Also preferred are the mature forms of such proteins, ie. from residues 28 onwards.

Particular amino acids which may be altered in the protein sequence of Seq. ID No.2 or Seq. ID No. 3 include alterations at any positively charged residue, eg. lys or arg, and/or at any negatively charged residue, eg asp or glu. The residues of Seq. ID. No. 2 which may be altered thus include: 29(asp), 41(arg), 50(asp), 53(glu), 60(lys), 68(lys), 69(arg), 71(arg), 76(asp), 79(glu), 80(glu), 84(lys), 87(asp) or 90(glu). The changes made to these positions may be as described above.

Combinations of changes which may be made include changing the final 2, 3, 4, 5 or 6 charged residues of the stem cell inhibitor. In the came of the human protein, this results in a protein which corresponds to the native protein except for changes at position 90 and/or one or more of positions 76, 79, 80, 84 or 88. Preferably, all the changes are single amino acid substitutions. Preferably, all such substitutions are conservative changes.

Proteins according to the invention may be made by any means available in the art. In the examples which follow, we have made modified stem cell inhibitory proteins by site directed mutagenesis using PCR primers of the murine SCI cDNA, followed by expression of the modified cDNA in a vector in a host cell to produce the protein. The protein may be recovered from the host cell using protein purification techniques known per se. Analogous methods may be used to make modified human or other primate SCI. The murine cDNA may be obtained for example by reference to the methods disclosed in WO89/10133 or by reference to the published literature. Human cDNA may also be obtained by reference to the published literature or cloned using probes based on all or part of the DNA sequence of Seq. ID No. 1 to identify SCI cDNA in a cDNA library made from cells expressing SCI RNA.

Accordingly, the present invention also provides a method for making a protein according to the invention which comprises:

(i) modifying a DNA sequence coding for SCI protein in order to introduce at least one change which causes a change in the amino acid sequence of the SCI protein;

(ii) expressing said DNA, operably linked to a promoter, in a vector in a host cell compatible with said promoter; and (iii) recovering said protein.

The DNA may be modified by site directed mutagenesis as mentioned above or described in the examples, to obtain insertions, deletions or subsitutions in the amino acid sequence.

The vector may contain one or more selectable marker genes, for example an ampicillin resistance gene in the case of a bacterial plasmid or a neomycin resistance gene for a mammalian vector.

A further embodiment of the invention provides host cells transformed or transfected with the vectors for the replication and expression of DNA produced as described above, including the DNA Seq. ID No. 1 modified as mentioned above. The cells will be chosen to be compatible with the vector and may for example be bacterial, yeast, insect or mammalian.

The invention also provides monoclonal or polyclonal antibodies to a peptide according to the invention which is directed to a epitope containing an alteration of the native SCI. The invention further provides a process for the production of such monoclonal or polyclonal antibodies. Monoclonal antibodies may be prepared by conventional hybridoma technology using the proteins or peptide fragments thereof, as an immunogen. Polyclonal antibodies may also be prepared by conventional means which comprise inoculating a host animal, for example a rat or a rabbit, with a peptide of the invention and recovering immune serum.

In either case, antibodies which recognise altered epitopes may be identified by screening them with native SCI and the altered SCI to which the antibody was raised and identifying an antibody which recognises only the altered SCI.

The following examples illustrate the invention.

EXAMPLE 1

FIG. 1 shows a schematic representation of murine SCI/MIP1-α indicating the position of charged amino acids. A series of altered proteins (1)–(3) were made using PCR primers on cDNA encoding the protein together with a wild type 5' primer. The altered proteins all contained conservative changes, ie. glutanmate to glutamine and/or aspartate to asparagine. The primers used are as follows:

Variant 1:
5' TC AGG AAT TCA GGC ATT CAG TTG CAG GTC 3' (SEQ ID NO. 4). This alters the C-terminal end of the murine MIP1-α protein from: VQEYITDLELNA (SEQ ID NO. 5) to VQEYITDLQLNA (SEQ ID NO.6).

Variant 2:
5'TC AGG AAT TCA GGC ATT CAG TTG CAG GTT AGT GAT 3' (SEQ ID NO.7) which alters Seq. ID No. 5 to VQEYITNLQLNA (SEQ ID NO.8).

Variant 3:
5' TC AGG AAT TCA GGC ATT CAG TTG CAG GTT AGT GAT GTA TTG TTG GAC 3' (SEQ ID NO. 9) which alters Seq. ID No. 5 to VQQYITNLQLNA (SEQ ID NO.10)

The varied cDNA molecules were ligated into a fusion protein expression vector and the altered proteins were produced. The native protein together with the three altered proteins were analysed by chromatographic techniques and the molecular weights of each estimated.

The estimates were as follows:

| Native protein | 100–150 kD |
|---|---|
| Protein (1) | 35 kD |
| Protein (2) | 18 kD |
| Protein (3) | 8 kD |

Protein (1) thus appears to exist as a tetramer, protein (2) as a dimer and protein (3) as a monomer under conditions in which native MIP1-α exists as an aggregated protein.

The above proteins were assesed for bioactivity using standard techniques (Pragnell et al Blood, 1998, 72; 196 and Lorimore et al, 1990, Leukaemia Research 14; 481) and found to be bioactive.

EXAMPLE 2

Two 3' (carboxy terminus) primers were synthesised with the following sequences:

5' GTA CGT GGA TCC TCA GGC ACT CAG CTG CAG GTT GCT GAC ATA TTG CTG GAC 3' (SEQ ID NO. 11)

and

5' GTA CGT GGA TCC TCA GGC ACT CAG CTG CAG GTT GCT GAC ATA TTG CTG GAC CCA CTG CTC ACT 3' (SEQ ID NO. 12).

A Bam H1 recognition site is underlined.

The primer of Seq. ID No. 11 encodes amino acids 82 to 93 of Seq. ID No. 1 but alters the lysine at position 84 (84(lys)) to glutamine (gln), 88(asp) to asn, and 90(glu) to gln.

The primer of Seq. ID. No. 12 encodes to amino acids 78 to 93 of Seq. ID No. 1 but contains the three changes described above for Seq. ID No. 11 and also a futher change, 80(glu) to gln.

To produce the human variants incorporating the above changes the above primers are each used with an amino terminal primer of Seq. ID No. 13:

5' GAC GGC CAT GGC TGA CAC GCC GAC CGC CTG C 3' (SEQ ID NO. 13) which encodes amino acids 28–35 of Seq. ID No. 1. An Ncol recognition site is underlined. This corresponds to the start of the mature SCI/MIP-1 protein.

The primers are used in a PCR to provide full length clones encoding variants incorporating the changes described above, and the variant clones introduced into an expression vector to provide dissagregated variant proteins of the invention.

The variants are tested in a similar manner as described above for activity.

EXAMPLE 3

A internal primer which encodes a central portion of the murine MIP1-α protein was designed, incorporating changes which cause point mutations in two of the three positively charged residues between the third and fourth cysteine residues shown in FIG. 1(a). The primer is of the sequence:

5' CGT CTA GAC GGC CAA CGA CAA TCA GTC CTT 3' (SEQ ID NO. 14) which alters the murine sequence:

FLTKRNRQIC (SEQ ID NO. 15) to FLTNSNRQIC (SEQ ID NO. 16).

The mutagenesis was done in two halves using this primer and the wild type amino termial primer and a complemetary primer was used with the wild type carboxy terminal primer. The two reaction products were then mixed and the full length molecule produced using the wild type amino and carboxy terminal primers. The variant is also tested for activity.

---

We claim:

1. A protein having stem cell inhibitory activity and having an amino acid sequence comprising the sequence of SEQ ID NO:2 from amino acid 28 to amino acid 93 with at least one amino acid substitution at an amino acid selected from the group consisting of 29(asp), 41(arg), 50(asp), 53(glu), 60(lys), 68(lys), 69(arg), 71(arg), 76(asp), 79(glu), 80(glu), 84(lys), 88(asp) and 90(glu), which protein does not significantly aggregate.

2. A protein according to claim 1 which exists as a tetramer, dimer or monomer under conditions in which a protein having the amino acid sequence of SEQ ID NO:2 from amino acid 28 to amino acid 93 exists as an aggregate.

3. A protein according to claim 1 which contains 2 or 3 amino acid substitutions.

4. A pharmaceutical composition comprising a protein according to claim 1 in combination with a carrier or diluent.

5. A method for treating a subject who is to be exposed to an agent capable of killing dividing or cycling stem cells by administering to the subject an effective amount of a composition according to claim 4.

6. A method for making a protein according to claim 1 which comprises:

(i) expressing a polynucleotide encoding a protein of claim 1, operably linked to a promoter, in a vector in a host cell compatible with said promoter; and (ii) recovering said protein.

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 282 base pairs (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION: 1..282

(xi) SEQUENCE DESCRIPTION: SEQ ID NO:1:

```
ATG CAG GTC TCC ACT GCT GCC CTT GCC GTC CTC CTC TGC ACC ATG GCT      48
Met Gln Val Ser Thr Ala Ala Leu Ala Val Leu Leu Cys Thr Met Ala
1               5                   10                  15

CTC TGC AAC CAG GTC CTC TCT GCA CCA CTT GCT GCT GAC ACG CCG ACC      96
Leu Cys Asn Gln Val Leu Ser Ala Pro Leu Ala Ala Asp Thr Pro Thr
            20                  25                  30

GCC TGC TGC TTC AGC TAC ACC TCC CGA CAG ATT CCA CAG AAT TTC ATA     144
Ala Cys Cys Phe Ser Tyr Thr Ser Arg Gln Ile Pro Gln Asn Phe Ile
        35                  40                  45

GCT GAC TAC TTT GAG ACG AGC AGC CAG TGC TCC AAG CCC AGT GTC ATC     192
Ala Asp Tyr Phe Glu Thr Ser Ser Gln Cys Ser Lys Pro Ser Val Ile
    50                  55                  60

TTC CTA ACC AAG AGA GGC CGG CAG GTC TGT GCT GAC CCC AGT GAG GAG     240
Phe Leu Thr Lys Arg Gly Arg Gln Val Cys Ala Asp Pro Ser Glu Glu
65                  70                  75                  80

TGG GTC CAG AAA TAC GTC AGT GAC CTG GAG CTG AGT GCC TGA             282
Trp Val Gln Lys Tyr Val Ser Asp Leu Glu Leu Ser Ala *
                85                  90
```

(2) INFORMATION FOR SEQ ID NO:2:

(i) SEQUENCE CHARACTERISTICS:
        (A) LENGTH: 93 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala
                85                  90
```

(2) INFORMATION FOR SEQ ID NO:3:

(i) SEQUENCE CHARACTERISTICS:
        (A) LENGTH: 92 amino acids
        (B) TYPE: amino acid
        (D) TOPOLOGY: linear (ii) MOLECULE TYPE: protein (xi) SEQUENCE DESCRIPTION: SEQ ID NO:3:

```
Met Gln Val Ser Thr Ala Ala Leu Ala Val Leu Leu Cys Thr Met Ala
1               5                   10                  15
```

```
        Leu Cys Asn Gln Phe Ser Ala Ser Leu Ala Ala Asp Thr Pro Thr Ala
                    20                  25                  30

Cys Cys Phe Ser Tyr Thr Ser Arg Gln Ile Pro Gln Asn Phe Ile Ala
                    35                  40                  45

Asp Tyr Phe Glu Thr Ser Ser Gln Cys Ser Lys Pro Gly Val Ile Phe
                    50                  55                  60

Leu Thr Lys Arg Ser Arg Gln Val Cys Ala Asp Pro Ser Glu Glu Trp
         65                  70                  75                  80

Val Gln Lys Tyr Val Ser Asp Leu Glu Leu Ser Ala
                    85                  90
```

(2) INFORMATION FOR SEQ ID NO:4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
TCAGGAATTC  AGGCATTCAG  TTGCAGGTC                                          29
```

(2) INFORMATION FOR SEQ ID NO:5:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
        Val Gln Glu Tyr Ile Thr Asp Leu Glu Leu Asn Ala
         1               5                  10
```

(2) INFORMATION FOR SEQ ID NO:6:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
        Val Gln Glu Tyr Ile Thr Asp Leu Gln Leu Asn Ala
         1               5                  10
```

(2) INFORMATION FOR SEQ ID NO:7:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
TCAGGAATTC  AGGCATTCAG  TTGCAGGTTA  GTGAT                                  35
```

(2) INFORMATION FOR SEQ ID NO:8:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Val Gln Glu Tyr Ile Thr Asn Leu Gln Leu Asn Gln
    1               5                   10

(2) INFORMATION FOR SEQ ID NO:9:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

TCAGGAATTC AGGCATTCAG TTGCAGGTTA GTGATGTATT GTTGGAC                47

(2) INFORMATION FOR SEQ ID NO:10:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Val Gln Gln Tyr Ile Thr Asn Leu Gln Leu Asn Ala
    1               5                   10

(2) INFORMATION FOR SEQ ID NO:11:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GTACGTGGAT CCTCAGGCAC TCAGCTGCAG GTTGCTGACA TATTGCTGGA C            51

(2) INFORMATION FOR SEQ ID NO:12:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

GTACGTGGAT CCTCAGGCAC TCAGCTGCAG GTTGCTGACA TATTGCTGGA CCCACTGCTC   60

ACT                                                                63

(2) INFORMATION FOR SEQ ID NO:13:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:13:

GACGGCCATG GCTGACACGC CGACCGCCTG C                                      31

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

CGTCTAGACG  GCCAACGAC AATCAGTCCTT                                       30

(2) INFORMATION FOR SEQ ID NO:15:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Phe Leu Thr Lys Arg Asn Arg Gln Ile Cys
    1               5                   10

(2) INFORMATION FOR SEQ ID NO:16:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Phe Leu Thr Asn Ser Asn Arg Gln Ile Cys
    1               5                   10